(12) United States Patent Wood et al.

(10) Patent No.: US 7,592,144 B2
(45) Date of Patent: Sep. 22, 2009

(54) BACTERIAL LIGAND-BINDING SENSOR

(75) Inventors: David W. Wood, Princeton, NJ (US); Georgios Skretas, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 317 days.

(21) Appl. No.: 11/082,642

(22) Filed: Mar. 17, 2005

(65) Prior Publication Data

US 2006/0211046 A1 Sep. 21, 2006

(51) Int. Cl.
*G01N 33/53* (2006.01)
*G01N 33/554* (2006.01)
*C07H 21/04* (2006.01)
*C07K 14/00* (2006.01)

(52) U.S. Cl. .................. 435/7.1; 435/7.8; 435/7.32; 536/23.4; 530/350

(58) Field of Classification Search ................ None
See application file for complete search history.

(56) References Cited

U.S. PATENT DOCUMENTS 7,192,739 B2* 3/2007 Liu et al. ............... 435/69.1
2004/0091966 A1* 5/2004 Zeidler et al. .......... 435/69.1

OTHER PUBLICATIONS

Aranda et al., 2001, Physiol. Rev. 81:1269-1304.
Azizi et al., 2003, Biochemical and Biophysical Research Communication, 306:744-780.
Belfort et al., 1984, J. Bacteriol. 160:371-378.
Bourguet et al., 2000, Trends Pharmacol. Sci. 21:381-388.
Buskirk et al., 2004, Proc. Natl. Acad. Sci. USA 101:10505-10510.
Carreras et al., 1995, Annu. Rev. Biochem. 64:721-762.
Chen et al., 2003, Gene 306:127-134.
Chen et al., 2004, J. Biol. Chem. 279:33855-33864.
Coward et al., 2001, Proc. Natl. Acad. Sci. USA 98:8880-8884.
De Urquiza et al., 2000, Science 290:2140-2144.
Derbyshire et al., 1997, Proc. Natl. Acad. Sci. USA 94:11466-11471.
Drews, 2000, Science 287:1960-1964.
"Engineering Hormone-Sensitive Bacteria: A Step Further Towards Efficient Drug Screening," Conference Presentation, AICHE 2003 Annual Meeting, San Francisco, CA, Nov. 16, 2003.
"Engineering Hormone-Sensitive Bacteria: A Step Further Towards Efficient Drug Screening," Poster Presentation, Mid-Atlantic Biochemical Engineering Consortium, Baltimore County, MD, Mar. 22, 2004.
Fang et al., 2000, Environmental Health Perspectives, 108:723-729.
Fitzsimons-Hall et al., 2002, J. Mol. Biol. 323:173-179.
Gangopadhyay et al., 2003, Biochim. Biophys. Acta 1619:193-200.
Giguere, 1999, Endocr. Rev. 20:689-725.
"An Introduction to Protein Splicing," web page accessed at www.neb.com/inteins/intein_bkgd.html on Mar. 2, 2005.
Israel et al., 1993, Proc. Natl. Acad. Sci. USA 90:4290-4294.
Joyeux et al., 1997, Anal. Biochem., 249:119-130.
Kamei et al., 2003, Proc. Natl. Acad. Sci. USA 100:12378-12383.
Kapust et al., 1999, Protein Sci. 8:1668-1674.
Kliewer et al., 1998, Cell 92:73-82.
Kuiper et al., 1997, Endocrinology 138:863-870.
Liu et al., 1999, Biol. Chem. 380:1341-1345.
Mattioni et al., 1994, Methods Cell Biol. 43(Pt A):335-352.
"Mtu-H37Rv RecA Intein," In: InBase, Perler 2002, Nucl. Acids, Res. 30:383-384.
Paulus, 2003, Front. Biosci. 8:s1157-s1165.
Pham et al., 1991, Proc. Natl. Acad. Sci. USA 88:3125-3129.
Picard, 2000, Methods Enzymol. 327:385-401.
Power et al., 1990, J. Biol. Chem. 265:1419-1424.
Pratt et al., 1997, Endocr. Rev. 18:306-360.
"Protein Splicing Mechanism," web page accessed at www.neb.com/inteins/int_mech.html on Mar. 2, 2005.
"Purification Tricks for Recombinant Proteins," web page accessed at www.bio.mtu.edu/campbell/purifica.htm on Mar. 2, 2005.
Riggs et al., 2003, N. Engl. J. Med. 348:618-629.
Skretas et al., 2005, Protein Sci. 14:523-532.
Soto et al., 1995, Environ. Health Perspect. 103(Suppl 7):113-122.
Srinivasan, 1992, Mol. Endocrinol. 6:857-860.
Stehlin-Gaon et al., 2003, Nat. Struct. Biol. 10:820-825.
Stoddard et al., 1998, Nat. Struct. Biol. 5:3-5.
Takeda et al., 1995, J. Clin. Endocrinol. Metab. 80:2033-2040.
Tucker et al., 2001, Nat. Biotechnol.19:1042-1046.
Wittliff et al., 1990, J. Biol. Chem. 265:22016-22022.
Wood et al., 1999, Nat. Biotechnol., 17:889-892.
Wooge et al., 1992, Mol. Endocrinol. 6:861-869.
Wu et al., 2002, Nucleic Acids Res. 30:4864-4871.
Zacharewski, 1997, Environ. Sci. & Technol. 31:613-623.

* cited by examiner

*Primary Examiner*—Manjunath N Rao
*Assistant Examiner*—Shulamith H Shafer
(74) *Attorney, Agent, or Firm*—Duane Morris LLP; Gary D. Colby (57) ABSTRACT

The invention relates to fusion proteins and bacteria encoding them. The fusion proteins include a ligand-binding domain interposed between the splicing domains of an intein. An auxotroph-relieving protein domain is fused to one of the splicing domains so that the auxotroph-relieving function of the domain is activated upon ligand binding. The fusion proteins can be expressed in bacterial cells and used as sensors of binding of compounds with the ligand-binding domain of proteins such as the human estrogen receptors or the human thyroid hormone receptor. The bacterially expressed fusion proteins can detect and report agonist and antagonist activity characteristic of the naturally-occurring hormone with the ability to modulate the function of the protein from which the ligand-binding domain of the fusion protein is derived.

26 Claims, 8 Drawing Sheets

BACTERIAL LIGAND-BINDING SENSOR

STATEMENT REGARDING FEDERALLY SPONSORED RESEARCH OR DEVELOPMENT

This work was supported in part by a grant from National Science Foundation (NSF CAREER Award Grant No. BES-0348220 and the U.S. Government may therefore have certain rights in this invention.

BACKGROUND OF THE INVENTION

The invention relates generally to the fields of biosensors and drug screening.

Many proteins exhibit altered properties upon binding of a specific ligand with a specialized domain of the protein. Such specialized domains are generally referred to as "ligand binding domains" (LBDs). The details of the mechanism by which ligand binding alters the properties of a protein are not well understood for all ligand binding-modulated proteins. Nonetheless, it is known that, for many such proteins, binding of a ligand with a LBD alters the three-dimensional conformation of the protein such that the conformation of another domain (i.e., one distinct from the LBD) of the protein is altered in a way that affects the catalytic or binding characteristics of the domain. By way of example, nuclear hormone receptors such as the estrogen receptor are activated upon ligand binding such that the activated receptor can modulate gene expression.

The nuclear hormone receptors are a family of ligand-activated eukaryotic transcription factors that control the expression of genes in response to the presence of small-molecule hormones or hormone-like compounds (Aranda et al., 2001, Physiol. Rev. 81:1269-1304). The estrogen, androgen, thyroid hormone, progesterone and vitamin D receptors are some well known members of this receptor superfamily. They comprise a very important class of drug targets, as their function has been linked to a broad spectrum of diseases, including breast, endometrial and prostate cancer, leukemia, cardiovascular diseases, osteoporosis and inflammations (Bourguet et al., 2000, Trends Pharmacol. Sci. 21:381-388; Riggs et al., 2003, N. Engl. J. Med. 348:618-629). Approximately 2% of the drug targets of current therapies belong to this receptor superfamily (Drews, 2000, Science 287:1960-1964), while 10% of the prescribed drugs are intended to modulate the function of those transcription factors. Discovery of novel compounds with the ability to modulate these targets is an important goal for the pharmaceutical industry.

Currently used screening strategies for identifying novel compounds with hormone-mimicking properties include in vitro competitive binding assays with radiolabeled hormones, transcriptional activation assays with various reporter proteins in *Saccharomyces cerevisiae*, and animal cell proliferation assays (Joyeux et al., 1997, Anal. Biochem. 249:119-130; Zacharewski, 1997, Environ. Sci. Technol. 31:613-623). One such example is the E-screen, where monitoring of the proliferation of human breast cancer cells in the presence of test compounds is used to evaluate their estrogenicity (Soto et al., 1995, Environ. Health Perspect. 103(Suppl 7):113-122). These screening approaches are generally complex, time-consuming, and expensive. There is a need for simpler, cheaper, and more rapidly performable assays for lead identification and characterization.

Naturally-occurring proteins often exhibit high binding specificity. Proteins which bind specifically with a particular ligand can therefore be used as a sensor or detector for the ligand if ligand binding can be observed. Furthermore, in the field of pharmacology, it is desirable to identify compounds that can interact with the LBD of a protein involved in a biological process, all the more so if the consequence of binding of the compound with the LBD can be detected. If the compound identification process can be performed rapidly and inexpensively, then collections of many compounds can be screened to identify individual compounds and types of compounds effective for modulating the biological process. Furthermore, if the detection method can be linked to a screenable or selectable phenotype in growing cells, then it can facilitate evolution of new drug compounds that have not been detected in any natural product.

The present invention satisfies these and other needs in the art by providing a method of assessing ligand binding that is relatively simple, cheap, and physiologically relevant.

BRIEF SUMMARY OF THE INVENTION

The invention relates to a fusion protein useful for detecting binding between a compound and a ligand-binding domain (LBD) of a protein. The fusion protein has the ligand-binding domain fused between the amino- and carboxyl-terminal splicing regions of an inactivated intein, preferably in place of at least most of the endonuclease domain of the naturally-occurring form of the intein (e.g., the Mtu RecA intein). A bacterial auxotroph-relieving protein domain (ARPD) is activatably fused to one of the splicing regions of the intein. Preferably, the LBD is fused to the carboxyl-terminal end of the amino-terminal splicing region of the intein and to the amino-terminal end of the carboxyl-terminal splicing region of the intein and the ARPD is fused to the carboxyl-terminal end of the carboxyl-terminal splicing region of the intein.

The protein from which the LBD is obtained or derived can, for example, be a membrane-bound receptor protein. Alternatively, the LBD can be obtained or derived from a nuclear receptor protein, such as a nuclear hormone receptor protein. Suitable proteins include estrogen receptors (e.g., human estrogen receptor alpha or beta) and thyroid hormone receptors (e.g., human thyroid hormone receptor beta).

Suitable ARPDs include functional domains of a protein required for a function such as purine uptake, purine metabolism, pyrimidine uptake, pyrimidine metabolism, amino acid uptake, or amino acid metabolism. Examples of suitable ARPDs include a functional domain of dihydrofolate reductase and thymidylate synthase.

In the fusion protein, a solubility-enhancing protein domain can be fused to the splicing region of the intein to which the bacterial auxotroph-relieving protein domain is not fused. *E. coli* maltose-binding protein is an example of a suitable solubility-enhancing protein domain.

The invention also relates to polynucleotides that encode the fusion protein described herein, such as an expression cassette expressible in a bacterial cell. In such an expression cassette, a promoter/regulatory region operably linked with a coding region encoding the fusion protein.

Host bacteria can be transformed with vector expressibly encoding the fusion protein and used, for example in a method of assessing binding of a compound with a ligand-binding domain of a protein. In this method, the host bacterium is contacted with the compound in the presence of an auxotrophic medium. At least one trait of the bacterium (e.g., survival, growth, and proliferation) is observed. Exhibition of the trait in the presence of the compound is correlated with binding of the compound with the ligand-binding domain. Compounds acting as agonists or antagonists of binding of a known ligand of the LBD can be detected in a similar manner, by assessing the effect of the presence or concentration of the compound on the observed trait.

Methods such as those described herein can be used to compare the ability of a plurality of sequence variants of a ligand-binding domain to bind a ligand. In these methods, fusion proteins are separately expressed in populations of auxotrophic host bacteria, and at least one trait of the bacteria is observed. Exhibition of the trait in the presence of the compound is correlated with binding of the compound with the ligand-binding domain variant. By iteratively assessing the ability of a ligand to bind with a variant and altering the sequence of the variant, the ability of the LBD to bind a ligand can be altered.

BRIEF SUMMARY OF THE SEVERAL VIEWS OF THE DRAWINGS

FIG. 1 consists of FIGS. 1A and 1B. FIG. 1A is a trio of diagrams that illustrate the genetic constructs used to make the fusion proteins described herein. FIG. 1A-1 illustrates the arrangement of elements in the pMIT::ER plasmid. FIG. 1A-2 illustrates the arrangement of elements in the pMIT::ER* plasmid. FIG. 1A-3 illustrates the arrangement of elements in the pMIT::TR* plasmid. In FIG. 1A, the following abbreviations are used: $P_{tac}$=artificial tac promoter, an asterisk denoting a G to A base pair mutation present in hormone dependent phenotypes; MBP=maltose binding protein; N-Mtu=the first 96 amino acid residues of the Mtu RecA intein; C-Mtu,=the last 41 amino acid residues of the Mtu RecA intein; ER=human estrogen receptor alpha ligand-binding domain; TR=human thyroid hormone receptor beta ligand-binding domain; TS=T4 thymidylate synthase enzyme.

FIG. 2 consists of FIGS. 2A, 2B, 2C, and 2D.

FIG. 3, comprising In FIG. 3, A means no ligand; B means diethylstilbestrol; C means hexestrol; D means dienestrol; E means 4-hydroxytamoxifen; F means 17-beta-estradiol; G means estrone; H means 17-alpha-estradiol; I means tamoxifen; J means chlomiphene; K means bisphenol A; L means $T_3$ (3,3',5'-triiodo-L-thyronine); M means Triac (3,3',5-triiodothyroacetic acid); and N means progesterone. Each compound was added at a concentration of 10 micromolar. The numbers above the growth bars represent the relative binding affinity of each compound for the ER (17-beta-estradiol is arbitrarily set to 100) as reported by Kuiper et al., 1997, Endocrinology 138: 863-870. Experiments were carried out in triplicate and the error bars represent one standard deviation from the mean value.

FIG. 4 is a graph showing antagonism of estrogen agonists and antagonists. E. coli D1210(delta)thyA cells harboring pMIT::ER* were grown in the presence of 10 micromolar $E_2$ and increasing concentrations of known estrogen agonists (grey), estrogen antagonists (black), or a thyroid hormone agonist (clear). Relative cell growth was determined by $OD_{600}$ at 15 hours in 5 milliliter cultures of liquid thymineless medium at 34 degrees Celsius.

DETAILED DESCRIPTION OF THE INVENTION

The invention relates to fusion proteins that act as sensors of binding between a ligand-binding domain of a protein and its corresponding ligand(s). The fusion proteins can be expressed in bacterial systems and therein used as sensors of binding between the ligand-binding domain and a corresponding ligand. Because bacterial cells can often be grown more quickly, simply, and cheaply than eukaryotic cells or archaebacterial cells, sensor systems involving the bacterial sensors described herein can offer a number of advantages over previous sensing platforms.

The fusion proteins described herein have the ligand-binding domain (LBD) of a protein (e.g., a human hormone membrane receptor LBD) fused between the amino- and carboxyl-terminal splicing domains of an intein. The LBD can replace some or (preferably) substantially all of the endonuclease domain of the intein. One splicing domain of the intein (preferably the carboxyl-terminal splicing domain) is also fused to a functional portion of a protein capable of relieving a particular bacterial auxotrophy. The fusion protein is expressed in the bacterial auxotroph and, in the presence of an auxotrophic medium containing a ligand that specifically binds with the LBD, relieves the auxotrophy of the bacterium, permitting the bacterium to grow. Growth of the bacterium is thus an indication that the auxotrophic medium (or a sample added to it) contains a ligand recognized by the LBD. Similarly, if a compound added to the auxotrophic medium decrease auxotrophy relief by a known ligand of the LBD, that is an indication that the compound is an antagonist of the LBD.

The invention includes at least fusion proteins, polynucleotides encoding such fusion proteins, bacteria expressing the fusion protein, and methods of making and using each of these.

Definitions

As used herein, each of the following terms has the meaning associated with it in this section.

A fusion protein is a polypeptide generated by expression of a polynucleotide coding sequence that is made up of at least two in-frame coding regions that do not naturally occur together.

An inactivated intein is an intein having an amino acid sequence that has been altered such that the ability of the intein to cleave and splice a polypeptide in which the intein occurs has been substantially eliminated. The conserved sequences necessary for cleavage and splicing of inteins are known in the art (e.g., Chong et al., 1996, J. Biol. Chem. 271:22159-22168; Xu et al., 1996, EMBO J. 15:5146-5153; Stoddard et al., 1998, Nat. Struct. Biol. 5:3-5).

A ligand-binding domain of a protein is a part of a protein having chemical properties and a conformation in the native protein that confers to the domain the ability to bind with a compound (normally a compound much smaller than the protein) with the specificity normally associated with binding between a protein receptor and its corresponding ligand.

A bacterial auxotroph is bacterium or a strain of bacteria that has lost the ability to synthesize one or more substances required for its growth and metabolism. Common bacterial auxotrophs are bacterial strains which have been rendered (e.g., through mutation) unable to grow in the absence of a particular purine, pyrimidine, or amino acid.

An auxotrophic medium is a bacterial growth medium in which an bacterial auxotroph will not grow unless a substance required for growth and metabolism of the auxotroph is added to the medium.

An auxotroph-relieving protein domain is a portion of a protein (including the entire protein) that enables a bacterial auxotroph in an auxotrophic medium to grow more rapidly when the domain is expressed in the form of a protein or fusion protein by the auxotroph than when the domain is not expressed.

An auxotroph-relieving protein domain is activatably fused to a ligand-binding domain of a protein when a fusion protein in which the auxotroph-relieving protein domain is fused to the ligand-binding domain in such a manner that the auxotrophy-relieving function of the domain is greater when a ligand is bound to the ligand-binding domain than when a ligand is not bound to the ligand-binding domain.

DETAILED DESCRIPTION

The invention includes fusion proteins that can be used in a bacterial setting to detect ligands, agonists, and antagonists of a ligand-binding domain (LBD) of an LBD-containing protein. In the fusion protein, the LBD is fused between the amino- and carboxyl-terminal splicing domain of an inactivated intein. A functional domain of a protein that can relieve a bacterial auxotroph is also fused to one of the splicing domains. The arrangement and connection of the fused LBD, intein splicing domain, and auxotroph-relieving protein domain are selected such that binding of a ligand with the LBD activates the auxotroph-relieving function of the protein domain. In this way, ligand binding can be detecting by observing bacterial growth on or in an auxotrophic medium.

Fusion proteins described herein can be expressed in auxotrophic bacteria. Because the bacteria will not grow in a corresponding auxotrophic medium (e.g., thymine auxotrophs will not grow in a medium lacking thymine), their growth can be used as an indicator that binding occurs between a component of (or a component added to) the medium and the LBD of the fusion protein. Such bacterial systems can be used to assess binding of potential ligands with the LBD, agonism between compounds and the LBD, antagonism between compounds and the LBD, or the effect of altering the amino acid sequence of the LBD on ligand-binding specificity, for example.

The ease with which bacteria can be grown and observed make this a favorable system for investigating binding between compounds and an LBD. The fact that systems such as those described herein also exhibit the agonism and antagonism characteristics of binding partners of the protein from which the LBD is derived also render them suitable for such purposes, because the results obtained using these systems is likely to closely mirror behavior of the LBD in its physiological setting. These characteristics make the system suitable for use both in individual assays and in high-throughput screening applications, such as pharmaceutical lead compound discovery and development, engineering of LBDs, and determination of function of uncharacterized LBDs and LBD-containing proteins.

Fusion Proteins

The fusion proteins described herein include at least four domains: i) a ligand-binding domain (LBD); ii) the amino-terminal splicing region of an intein; iii) the carboxyl-terminal splicing region of the intein; and iv) an auxotroph-relieving protein domain (ARPD). The LBD is fused between the amino- and carboxyl-terminal splicing domains. The ARPD is fused with one of the amino- and carboxyl-terminal splicing domains. If necessary or desired, a solubility-enhancing protein domain (SEPD) can be included in the fusion protein as well, preferably at the amino-terminal end thereof.

In a preferred arrangement, the LBD is fused to the carboxyl-terminal end of the amino-terminal splicing region of the intein and to the amino-terminal end of the carboxyl-terminal splicing region of the intein and the ARPD is fused to the carboxyl-terminal end of the carboxyl-terminal splicing region of the intein. In this arrangement, a SEPD can optionally be fused to the amino-terminal end of the amino-terminal splicing region of the intein.

The protein domains can be fused directly one to another (i.e., with no intervening amino acid residues), or by way of relatively short linker sequences (e.g., linker regions consisting of 1 to about 40 amino acid residues). When linker sequences are used, they preferably have amino acid sequences which do not exhibit significant secondary, tertiary, or quaternary protein structures. Preferably, no linker sequence is included between the ARPD and the intein splicing region with which it is fused.

A variety of methods for making fusion proteins from known protein domains are described in the art and within the skill of the ordinary artisan in this field. Substantially any such method can be used to make the fusion proteins described herein and polynucleotides and bacterial expression constructs that comprise them. Likewise, methods of expressing fusion proteins in bacteria are known in the art and within the skill of the ordinary artisan in this field. Substantially any such method can be used to express the fusion proteins and use them in the methods described herein can be used, in view of the disclosure provided herein.

The Ligand-Binding Domain

The identity of the LBD of the fusion proteins described herein is not critical. What is important is to include in the fusion protein a sufficient length of the primary amino acid sequence of the LBD-containing protein from which the LBD is derived that the secondary and any tertiary structure of the protein that is necessary for functionality (i.e., ligand-binding ability) of the LBD is preserved in the fusion protein.

The functional LBD preferably does not depend significantly on the tertiary structure of the protein from which it is derived. It is recognized that many LBDs and protein subunits containing LBDs are able to bind their corresponding ligands as monomers. If the LBD of the fusion protein described herein requires an additional protein subunit, then that subunit must be expressed in the bacterium in which the fusion protein is expressed. The fusion protein described herein preferably does not include an LBD that depends for its functionality (i.e., its ligand binding activity) on the quaternary structure of the protein in which it occurs.

The LBD of the fusion protein is fused between the amino- and carboxyl-terminal splicing regions of an inactivated intein. The LBD can be fused in place of some or all of the endonuclease domain of the naturally-occurring form of the intein, and preferably replaces at least most of the endonuclease domain. If a portion of the endonuclease domain of the intein is retained, the portion should be selected such that it does not affect the ligand-binding properties of the LBD. In a preferred embodiment, the entire endonuclease domain is removed, and the LBD is fused in frame with each of the amino- and carboxyl-terminal splicing regions.

A wide variety of LBD-containing proteins are known. The LBD used in the fusion proteins described herein is preferably one which binds specifically with a relatively small compound, such as a hormone, small (<10mer) polypeptide, or small organic molecule (e.g., organic molecules having molecular weights <ca. 3000). LBDs which specifically bind larger ligands can be used, but it is recognized that steric hindrance of binding of relatively large ligands with the LBD of the fusion proteins described herein can occur, potentially limiting the usefulness of the compositions and methods described herein for detecting interactions between the LBD and very large or very bulky ligands.

Suitable LBDs for inclusion in the fusion proteins described herein include the LBDs of many proteins known to bind specific ligands. Examples of these proteins include numerous enzymes, regulators of DNA expression, nuclear receptor proteins, and membrane-bound receptor proteins. LBDs of several nuclear hormone receptor proteins are described in the examples herein. Nuclear hormone receptor proteins are ligand-activated transcription factors that mediate the effects of compounds (e.g., steroid hormones such as estrogen and thyroid hormone) on gene expression. Numerous nuclear hormone receptor proteins are known, including several for which no physiological function is yet known.

The LBDs of nuclear hormone receptor proteins have been shown to possess the ability to act as post-translational functional switches for a number of heterologous proteins when included as end-to-end or insertional fusions (Mattioni et al., 1994, Methods Cell Biol. 43(Pt A):335-352; Picard, 2000, Methods Enzymol. 327:385-401). LBDs derived from the estrogen, androgen, glucocorticoid, progesterone, mineralocorticoid, ecdysone and thyroid hormone receptors have been used to impart hormone-regulated activity to transcription factors, oncoproteins, kinases, recombinases, and other reporter proteins such as beta-galactosidase and dihydrofolate reductase (DHFR; Mattioni et al., 1994, Methods Cell Biol. 43(Pt A):335-352; Picard, 2000, Methods Enzymol. 327:385-401). This ability has been exploited to develop many of the currently used in vivo screening strategies for endocrine modulators and as a tool for deciphering aspects of a variety of different hormone-regulated endocrine pathways in higher eukaryotes (Joyeux et al., 1997, Anal. Biochem. 249:119-130). However, these properties have not previously been applied to construction of bacterial systems for high-throughput screening of test compounds.

An in vivo sensor of estrogen binding in yeast was recently developed that reports the presence of active compounds through a change in growth phenotype on selective medium (Tucker et al., 2001, Nat. Biotechnol. 19:1042-1046). That yeast-centered system is based on a chimeric fusion of the LBD of the human estrogen receptor with temperature-sensitive mutants of DHFR. DHFR-deficient yeast strains are able to grow at elevated temperatures only in the presence of estrogen, thus allowing compounds with estrogen-like properties to be identified. That sensor was able to successfully detect estrogen analogues from a small library of test compounds. However, a general limitation to yeast-based hormone-sensing systems has been their inability to recognize the biologically relevant role of a test compound. Yeast-based assays, for example, have been unable to reliably discriminate between agonistic and antagonistic effects of synthetic hormone mimics (Joyeux et al., 1997, Anal. Biochem. 249:119-130). The bacterial sensing systems described herein do not have that drawback.

The Auxotroph-Relieving Protein Domain

The ARPD of the fusion protein is activatably fused to a splicing region of the intein, such that upon binding of a ligand with the LBD the ARPD exhibits its auxotroph-relieving function at a level greater than the level exhibited in the absence of ligand binding. It is recognized that some limited amount of experimentation may be necessary to optimize the activatable fusion of the ARPD to the LBD by way of one of the intein splicing domains. Nonetheless, the necessity of such limited experimentation is typical in the field of operably connecting functional protein domains, and such experimentation is within the ken of the ordinarily skilled artisan in this field. Depending on the LBD, intein splicing domain, and ARPD selected, the domains can be directly fused to one another or a relatively short (e.g., 1-40 residues) linker sequence can be interposed between domains. When such a linker is used, the linker should be substantially devoid of secondary, tertiary, or quaternary protein structure. Preferably, there is no linker between the ARPD and the adjacent intein splicing domain.

The function of the ARPD is to provide a signal that binding between the LBD of the fusion protein and a ligand thereof has occurred. Auxotroph-relieving signals are preferred because they provide a simple detection method (i.e., observing growth versus no-growth or high versus low growth). Examples of suitable auxotroph-relieving proteins from which ARPDs can be obtained include proteins that have a required role in a function such as purine uptake, purine metabolism, pyrimidine uptake, pyrimidine metabolism, amino acid uptake, or amino acid metabolism. Two specific examples are thymidylate synthase and dihydrofolate reductase. The ARPD can include the entire protein, or a portion of the protein that exhibits the catalytic or transport activity of the protein upon activation by binding between the LBD of the fusion protein and a ligand thereof.

It is known that some auxotrophs exhibit auxotrophy only at certain temperatures. For example, *E. coli* thymine synthase knockout strains which express little or no thymidylate synthase enzyme (e.g., from an exogenous plasmid) are able to grow at relatively low temperatures at a rate similar to non-auxotrophs, but grow much more slowly at a higher temperature than non-auxotrophs.

Such temperature-dependent auxotrophs are useful for a number of reasons. First, the temperature-sensitive auxotrophs can be propagated in auxotrophic medium at low temperature. Also, replicate cultures can be grown at high and low temperature, the low temperature confirming that the bacterium containing the fusion protein was present, and the higher temperature indicating whether ligand binding occurred.

The Intein Splicing Domains

Inteins are protein domains which are known for their ability to excise themselves from a polypeptide in which they occur. A database of known inteins is maintained by New England Biolabs (Perler, 2002, Nucleic Acids Res. 30:383-384). Inteins generally consist of a central endonuclease-encoding domain flanked by two intein splicing domains. The splicing domains are designated the amino- and carboxyl-terminal splicing domains, based on their order of occurrence in protein sequences.

Inteins exhibit conserved amino acid residues and sequences, as described in the art (e.g., Perler, 2002, Nucleic Acids Res. 30:383-384). For example, several residues are known to be involved in splicing of inteins from polypeptides. Modification of those conserved residues in known ways can inactivate an intein, preventing the intein from excising itself from a polypeptide sequence. Furthermore, it is known that some or all of the endonuclease-encoding domain of an intein can be removed or replaced with an alternative protein-encoding sequence without affecting interaction and splicing of the splicing domains of the intein.

The intein domains used in the fusion proteins described herein are inactivated so that they do not excise themselves and the LBD that is fused between the intein splicing domains. Furthermore, most or all of the endonuclease-encoding sequence is preferably removed and replaced by a LBD as described herein.

The identity of the intein from which the intein splicing domains of the fusion proteins described herein is not critical. The splicing domains of substantially any intein can be used. Preferably, the splicing domains are derived from the same intein. If splicing domains from different inteins are to be used, the amino- and carboxyl-terminal intein splicing domains must assume the usual secondary structure of intein splicing domains (i.e., the secondary structure exhibited by splicing domains of a single naturally-occurring intein).

In the fusion proteins described in the examples provided herein, the intein splicing domains are derived from the Mtu RecA intein. However, the invention is not limited to that intein or its splicing domains. A skilled artisan in this field would understand that substantially any intein and its splicing domains can be employed.

Solubility-Enhancing Protein Domains

Not all eukaryotic proteins are soluble in the cytoplasm of bacterial cells when expressed in those cells. Solubility of proteins can be enhanced by fusing a relatively soluble protein or protein domain thereto, particularly if the protein or domain is fused to or near the amino terminus of the protein (i.e., such that the relatively soluble portion of the fused protein is translated first, "pulling" the fusion protein into solution).

The intein splicing domains of the fusion proteins described herein exhibit characteristic secondary and tertiary structure, the amino- and carboxyl-terminal splicing domains interacting with one another. Without being bound by any particular theory of operation, it is believed that the interacting amino- and carboxyl-terminal intein splicing domains serve to 'insulate' the secondary and tertiary protein structures of protein domains that occur i) on the amino-terminal side of the amino-terminal intein splicing domain; ii) between the amino- and carboxyl-terminal intein splicing domains; and iii) on the carboxyl-terminal side of the carboxyl-terminal intein splicing domain from one another, so that at least in the absence of LBD conformational changes induced by ligand binding, these protein domains do not significantly interact. So long as an intein splicing domain is interposed between the SEPD and the LBD, the SEPD should not affect the binding properties of the LBD. A relatively short linker sequence (e.g., 1-30 amino acid residues) can be interposed between the SEPD and the intein splicing domain to further insulate the LBD from the SEPD.

Substantially any hydrophilic domain of a protein or a soluble protein can be used as an SEPD. By way of example, E. coli maltose binding protein (MBP) is a highly soluble protein that has been used by others to enhance the solubility of fusion proteins. When a SEPD is included in the fusion proteins described herein, it should be fused to the end of the intein splicing domain—LBD—intein splicing domain construct that the ARPD is not fused to, and should preferably be fused at or near the amino terminus of the fusion protein.

Polynucleotides Encoding the Fusion Protein

The invention includes polynucleotides which encode a fusion protein described herein. A skilled artisan in this field is able to generate a large number of such polynucleotides, in view of the redundancy of the genetic code, the requirements for expression of a nucleotide sequence in a selected organism, and the multitude of genetic vectors and other constructs available for genetic manipulation of bacteria. Preferably, the polynucleotide includes a promoter/regulatory region operably linked with a coding region encoding the fusion protein, so that the protein can be expressed in a desired bacterium. The promoter/regulatory region can include a constitutive promoter, an inducible promoter, or any other known bacterial promoter. Genetic regions suitable for regulating expression of the fusion protein can also be included. By way of example, it has been discovered that including an E. coli lac operator region having a G to A substitution 16 bases downstream of the TATAA motif of the lac promoter enhances fusion protein production in at least some strains of E. coli.

Transformed Bacteria

The invention also includes a bacterium transformed with a polynucleotide from which the fusion protein described herein can be expressed. In preferred embodiments, the bacterium is either an auxotroph or a temperature-dependent auxotroph. By way of example, an E. coli strain which is capable of growth on thymineless medium at 18 degrees Celsius, but which is not capable of growth on the same medium at 34 degrees Celsius can be used.

Screening Methods for Assessing Ligands

Binding between a compound and the fusion protein described herein can be assessed in vitro if a detectable (e.g., calorimetric) assay exists or is made by which activity of the ARPD can be assessed. Such binding is preferably detected between the compound and the fusion protein expressed in vivo in a bacterium or other organism. When expressed in an auxotrophic bacterium, the fusion protein described herein can be used to assess the ability of a compound to bind with the LBD of the fusion protein. Such ability is assessed by contacting the bacterium with the compound and assessing the ability of the bacterium to grow, for example by observing colony formation of the bacterium on an auxotrophic medium containing the compound. Alternatively, the degree or extent of growth can be assessed, such as by assessing the turbidity or optical density of a liquid culture of the bacterium expressing the fusion protein in an auxotrophic medium containing the compound or by measuring colony size on a solid or semisolid auxotrophic medium containing the compound.

In a similar fashion, the ability of a second compound to modulate binding (i.e., as an agonist or antagonist) of a first compound with the LBD can be assessed by assessing growth of the bacterium in an auxotrophic medium containing both the first and second compounds.

Screening of LBDs

The screening methods described herein can be used to screen a plurality of sequence variants of a LBD of a fusion protein described herein for their ability to bind with a ligand. In these methods, a plurality of fusion protein having varying LBD sequences can be contacted with the ligand and plated or otherwise cultured in an auxotrophic medium. Bacteria expressing variants that bind with the ligand will survive, grow, and/or proliferate, and bacteria expressing variants that do not bind with the ligand will exhibit lesser survival, growth, and/or proliferation. Furthermore, bacteria harboring a first fusion protein that exhibits an LBD with greater binding affinity for the ligand than a second fusion protein can grow (survive, or proliferate) to a greater extent than bacteria harboring the second fusion protein. By selecting transformed bacteria based on the extent of survival, growth, or proliferation, LBDs with relatively high binding affinities can be obtained. Iterative screening and mutation steps can be performed to generate additional LBDs which can exhibit greater (or lesser) binding affinity.

EXAMPLE

A Bacterial Biosensor of Endocrine Modulators

The invention is now described with reference to the following example. This example is provided for the purpose of illustration only, and the invention is not limited to this example, but rather encompasses all variations which are evident as a result of the teaching provided herein.

In this example, thymine-auxotrophic *E. coli* bacteria were transformed with a genetic construct encoding a fusion protein including a thymidylate synthase (TS) moiety fused with a human hormone receptor protein ligand-binding domain (LBD) which was interposed between the amino- and carboxyl-terminal splicing regions of the Mtu RecA intein. An *E. coli* maltose binding protein moiety was also fused with the amino terminal splicing region of the intein. These fusion proteins were expressed in the transformed bacteria and relieved thymine auxotrophy in the presence of the corresponding hormone or agonists thereof. Antagonists of the receptor protein reduced auxotrophy relief.

In one set of experiments, the ligand-binding domain of the human estrogen receptor (ER) alpha, in combination with a stabilization and a solubilization domain, was fused to a TS enzyme. Expression of this fusion protein in TS-deficient *E. coli* strains resulted in specific hormone-dependent phenotypes, which could be readily detected through changes in cell growth on selective thymineless medium. Known hormone antagonists were able to neutralize the effects of known agonist compounds on cell growth when added in combination. These results indicate that the sensor protein is able to differentiate between agonistic and antagonistic activities.

In another set of experiments, the estrogen-sensing protein was converted to a thyroid hormone sensor by replacement of the ER domain with the ligand-binding domain of the human thyroid hormone receptor (TR) beta.

The information disclosed in this example can be used to construct bacterial hormone-binding sensors in substantially any bacterial species. Such systems are attractive alternatives for chemical library screening to identify lead molecules with potential therapeutic actions against serious diseases, and can also be applied to detection of environmental estrogens, pollutants, or other compounds that interfere with normal nuclear hormone receptor function. They also offer a facile tool for the evolution of peptide-based or other relatively small compound hormone mimics.

The materials and methods used in experiments corresponding to this Example are now described.

Reagents and Strains

All experiments were carried out using *E. coli* strains. DH5alpha (Invitrogen, Carlsbad, Calif.) and XL1-Blue (Stratagene, La Jolla, Calif.) cells were used for plasmid construction. Strain D1210(delta)thyA::Kan$^R$ [F$^-$delta(gpt-proA)62 leuB6 supE44 ara-14 galK2 lacY1 delta(mcrC-mrr) rpsL20 (Str$^r$) xyl-5 mtl-1 recA13 lacI$^q$] was used for the determination of growth phenotypes, as described (Derbyshire et al., 1997, Proc. Natl. Acad. Sci. USA 94:11466-11471).

The estrogen and thyroid hormone analogues 17-alpha-estradiol, 17-beta-estradiol, diethylstilbestrol, hexestrol, dienestrol, estrone, tamoxifen, 4-hydroxytamoxifen, 3,3',5'-triiodo-L-thyronine, and 3,3',5-triiodothyroacetic acid were purchased from Sigma (Saint Louis, Mo.). Chlomiphene, progesterone, and bisphenol A (4,4'-isopropylidenediphenol) were obtained from ICN Biomedicals (Aurora, Ohio). All compounds were dissolved in ethanol or dimethylsulfoxide (DMSO) to form 10 millimolar and 1 millimolar solutions. Progesterone was prepared as a 1 milligram per milliliter solution in ethanol.

Plasmid Construction

An artificial mini-intein was derived through the complete deletion of the native intein endonuclease domain between residues 96 and 400 of the full-length *Mycobacterium tuberculosis* RecA intein, as described (Derbyshire et al., 1997, Proc. Natl. Acad. Sci. USA 94:11466-11471). The first amino acid residue of the intein was changed from cysteine to alanine and of the ultimate residue was changed from asparagine to alanine. The coding sequence corresponding to residues Ser301-Thr553 of the human estrogen receptor alpha was amplified from the vector Gal4-ER-VP16 (a publicly available sequence, in this instance obtained from the Wadsworth Center, Albany, N.Y.). The coding sequence corresponding to residues Glu203-Asp461 of the human thyroid hormone receptor beta were derived from pCMV-hTRbeta (a publicly available sequence, in this instance provided by the Metabolic Research Unit, University of California, San Francisco, Calif.).

In each case, PCR primers were used to add a BssHII restriction site at each of the N- and C-termini of the ligand-binding domains. The LBDs of the estrogen and thyroid hormone receptors were inserted within the BssHII site of the mini-intein, as described (Derbyshire et al., 1997, Proc. Natl. Acad. Sci. USA 94:11466-11471). The sequences of the gene fusions were verified by nucleotide sequencing. The constructed fusions were cloned into pMal-c2 (New England Biolabs, Beverly, Mass.) as described (Wood et al., 1999, Nat. Biotechnol. 17:889-892).

Growth Phenotypes

Cells were grown overnight in LB medium containing 200 micrograms per milliliter ampicillin and supplemented with 50 micrograms per milliliter thymine. These saturated cultures were used with a 1:200 dilution to inoculate 5 milliliters of defined thymineless medium (Belfort et al., 1984, J. Bacteriol. 160:371-378) with 200 micrograms per milliliter ampicillin and selected concentrations of each of the hormone ligands. Stock solutions of hormone analogues in ethanol and DMSO were prepared to ensure a constant final concentration of organic solvent in phenotype tests. In all growth experiments, ethanol and DMSO concentrations were kept below 1%. Levels of cell growth were measured as $OD_{600}$ 12-20 hours after inoculation using a GENESYS (TM) 2 spectrophotometer. All experiments were carried out at least in duplicate.

The results of experiments corresponding to this Example are now described.

Design and construction of a hormone-sensing protein

The design of the hormone-sensing protein described in this example is based on coupling the hormone-dependent regulatory function of the ligand-binding domain of a nuclear receptor with the enzymatic activity of the well-characterized TS enzyme. The activity of this enzyme can be easily monitored by growth phenotype in TS-knockout cells (Belfort et al., 1984, J. Bacteriol. 160:371-378). The activity of TS has been used in several previously reported genetic selection systems (Derbyshire et al., 1997, Proc. Natl. Acad. Sci. USA 94:11466-11471; Wood et al., 1999, Nat. Biotechnol. 17:889-892). Because the amount of active TS required for growth increases rapidly with incubation temperature, this system provides a very sensitive, semi-quantitative measure of TS activity by simply testing growth phenotypes over a range of temperatures (Belfort et al., 1984, J. Bacteriol. 160:371-378; Derbyshire et al., 1997, Proc. Natl. Acad. Sci. USA 94:11466-11471; Wood et al., 1999, Nat. Biotechnol. 17:889-892). Furthermore, TS activity can be monitored by using a number of known chemical assays (Carreras et al., 1995, Annu. Rev. Biochem. 64:721-762).

Expression of human hormone-binding domains in E. coli is hampered by low yield, poor stability, and low solubility. These difficulties can be alleviated using various gene fusions (e.g., Srinivasan, 1992, Mol. Endocrinol. 6:857-860; Wooge et al., 1992, Mol. Endocrinol. 6:861-869; Wittliff et al., 1990, J. Biol. Chem. 265:22016-22022; Power et al., 1990, J. Biol. Chem. 265:1419-1424). The fusion proteins described in this example include stabilization and solubilization domains as parts of the constructed fusion.

The stabilization domain consisted of a previously isolated mini splicing domain of the *Mycobacterium tuberculosis* RecA intein (Mtu intein). Derivatives of this intein have been shown to fold properly and retain activity when inserted into different protein hosts (Paulus, 2003, Front. Biosci. 8:s1157-s1165) and can tolerate the genetic insertion of non-native short polypeptides (Gangopadhyay et al., 2003, Biochim. Biophys. Acta 1619:193-200) or entire folded protein domains (Wu et al., 2002, Nucleic Acids Res. 30:4864-4871; Fitzsimons-Hall et al., 2002, J. Mol. Biol. 323:173-179; Buskirk et al., 2004, Proc. Natl. Acad. Sci. USA 101:10505-10510; Skretas et al., 2005, Protein Sci. 14:523-532). Insertion of the hormone-binding domain of a nuclear receptor into minimal intein splicing domains allows the binding domain to adopt its correct fold and retain its binding characteristics in E. coli (Skretas et al., 2005, Protein Sci. 14:523-532). A maltose-binding protein (MBP) tag was also incorporated into the amino-terminal region of the fusion proteins described in this example in order to increase the solubility and activity of the chimeric fusion. Such stabilization has been observed with other fusion proteins (e.g., Kapust et al., 1999, Protein Sci. 8:1668-1674).

Figure 1A:
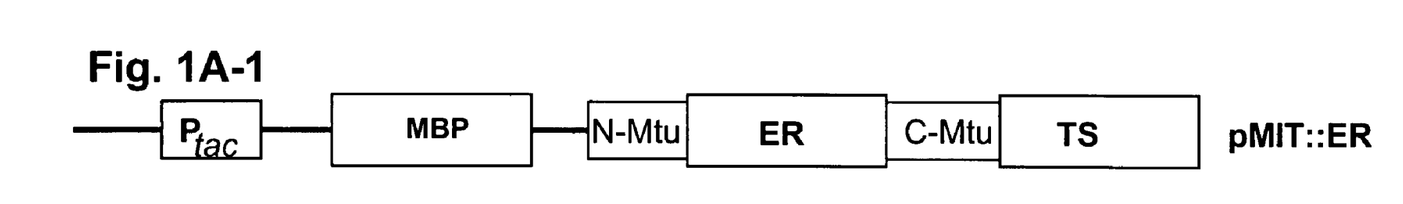

Following these guidelines, the endonuclease domain of the wild-type Mtu intein was replaced with the ER LBD to form our initial chimeric fusion. Splicing and amino-terminal cleavage by the intein were suppressed by mutation of its initial amino acid from cysteine to alanine, while carboxyl-terminal cleavage of the intein was prevented by substituting the ultimate asparagine residue with an alanine (Derbyshire et al., 1997, Proc. Natl. Acad. Sci. USA 94:11466-11471; Wood et al., 1999, Nat. Biotechnol. 17:889-892). The constructed chimeric intein was then fused to the amino-terminus of the bacteriophage T4 td gene (encoding the T4 TS enzyme), and the resulting fusion was cloned into plasmid pMal-c2 as a carboxyl-terminal fusion to the E. coli MBP. The T4 TS enzyme has been shown to complement TS-knockout bacterial cells, but the td gene will not recombine with the E. coli chromosomal thyA gene (Wood et al., 1999, Nat. Biotechnol. 17:889-892). The resulting plasmid is referred to as pMIT::ER (BP-Intein-TS::Estrogen Receptor; FIG. 1A-1).

Figure 1A:
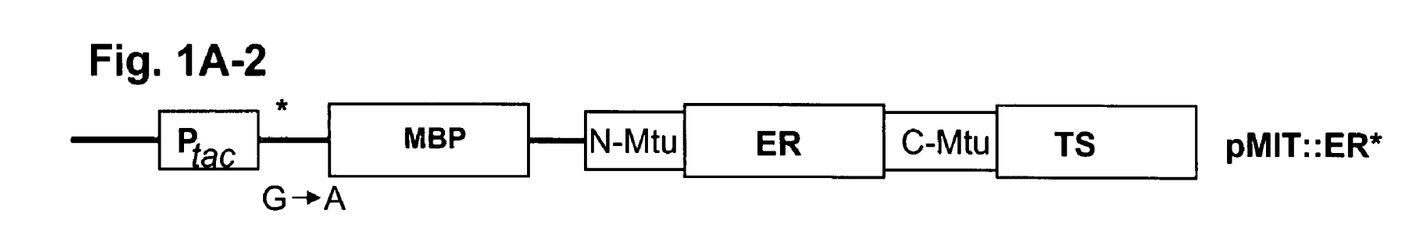
Figure 1A:
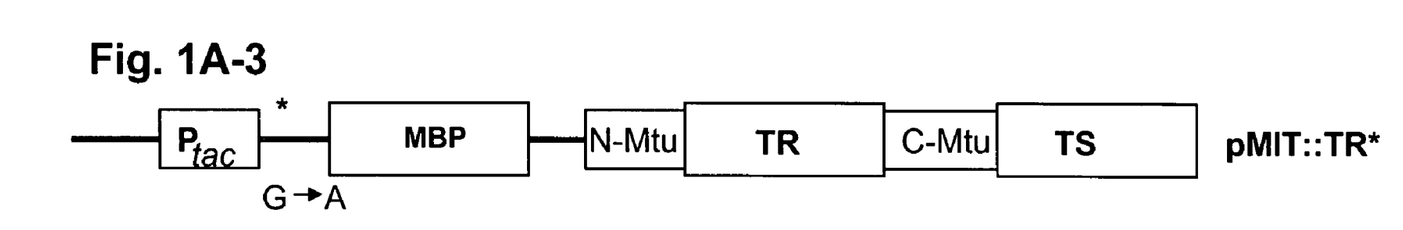
Figure 1B:
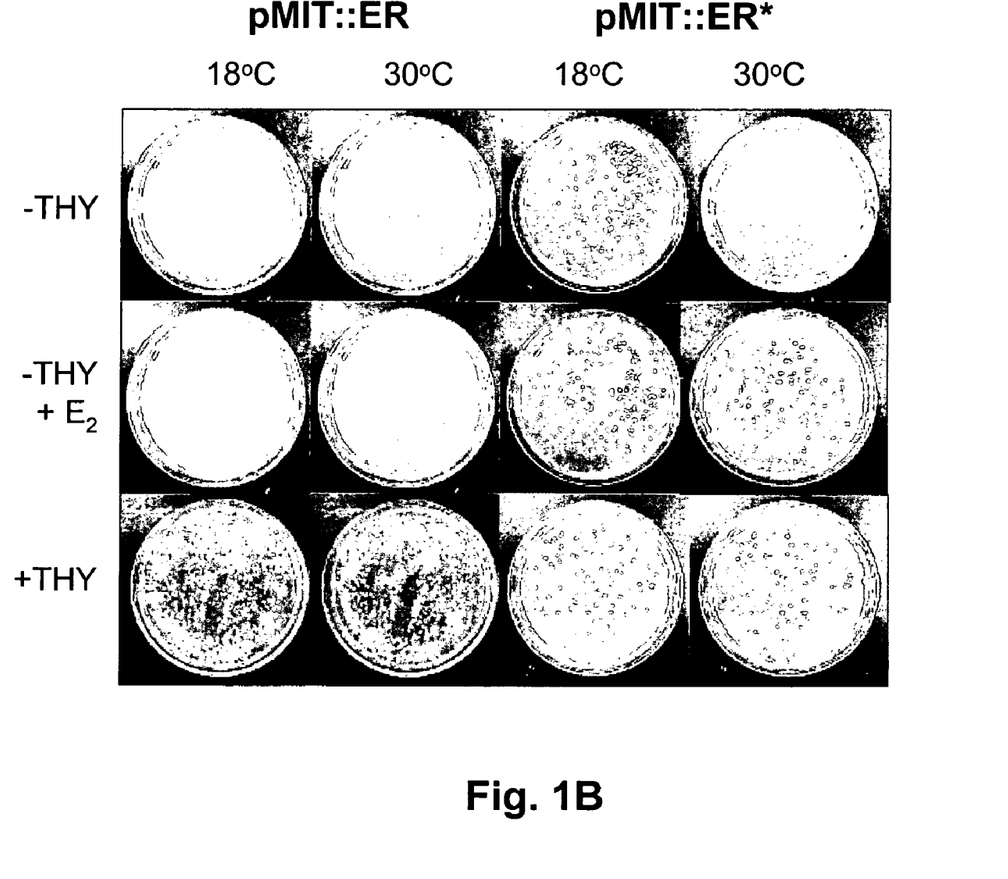
FIG. 1B is an image showing growth of E. coli D1210(delta)thyA cells transformed either with pMIT::ER or pMIT::ER* and incubated on thymineless agar plates for 70 hours at 18 degrees Celsius and 50 hours at 30 degrees Celsius in the absence (–THY) or presence of 50 micromolar 17-beta-estradiol (–THY+$E_2$). A thymine-rich medium (+THY) was used as a positive control.

E. coli D1210(delta)thyA cells, deficient in native TS, were transformed with pMIT::ER. The transformed cells were unable to grow in a medium lacking thymine at all temperatures (TS$^-$ phenotype), irrespective of the presence of estrogen, as shown in FIG. 1B. The pMIT::ER plasmid was introduced into E. coli XL1-Red for the introduction of random mutations that might impart hormone sensitivity. The resulting mutant library was then selected in E. coli D1210(delta)thyA for growth on thymineless agar plates (TS$^+$ phenotype) in the presence and absence of 17-beta-estradiol ($E_2$) at room temperature and at 30 degrees Celsius. Survivors appeared after 40 hours on all plates. However, colony formation was observed to become estrogen-sensitive on plates incubated at 30 degrees Celsius, as shown in FIG. 1B. Several of the mutants that exhibited TS$^+$ phenotypes were sequenced and all were found to contain a G to A nucleotide substitution in the lac operator region, 16 bases downstream of the TATAA motif of the tac promoter. Remarkably, no other mutations in the fusion protein coding sequence were detected, implying that the observed positive phenotype is based exclusively on changes in expression level, most likely due to reduced affinity of the lac repressor for this recognition sequence. One of the selected mutant plasmids was chosen for further characterization and is referred to as pMIT::ER* (asterisk indicates presence of operator mutation; FIG. 1A-2).

Hormone-Dependent Phenotypes

Figure 2A:
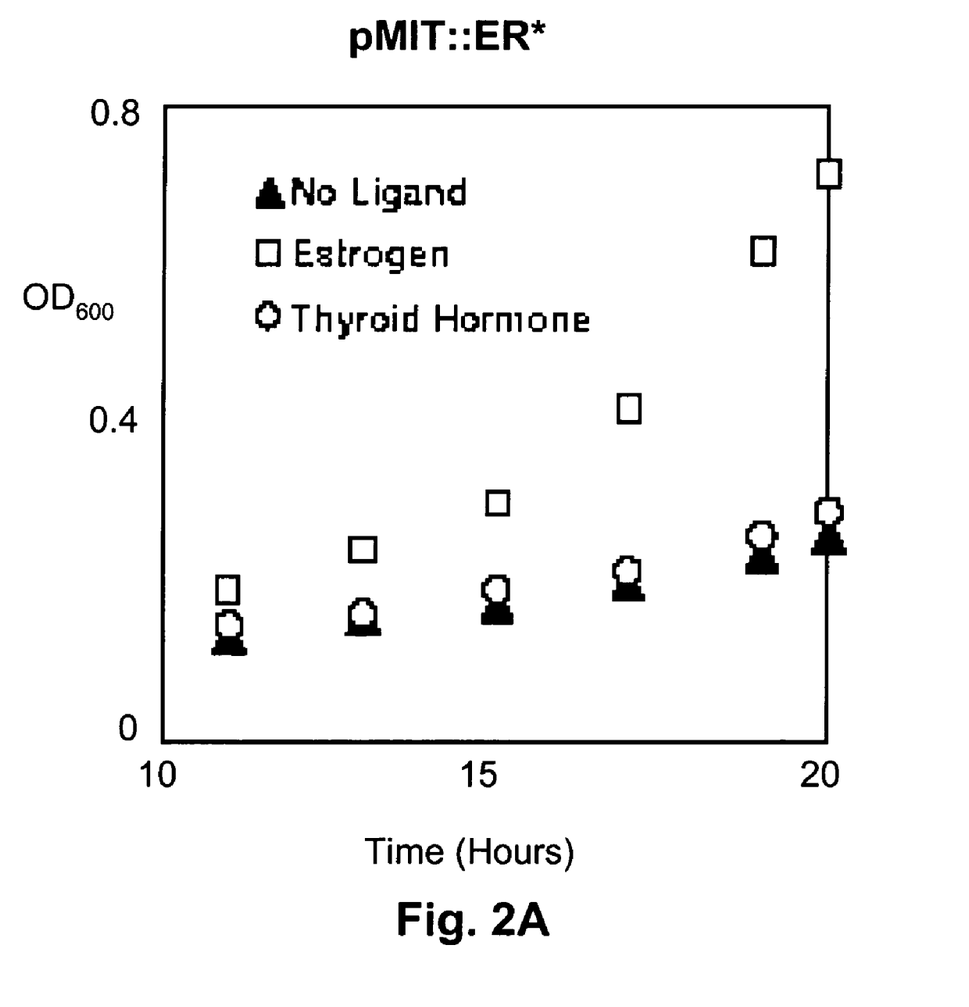
FIG. 2A is a graph that depicts ligand effects on the growth phenotypes of E. coli D1210(delta)thyA cells carrying the pMIT::ER* vector in 50 milliliter cultures of liquid thymineless medium at 34 degrees Celsius.
Figure 2B:
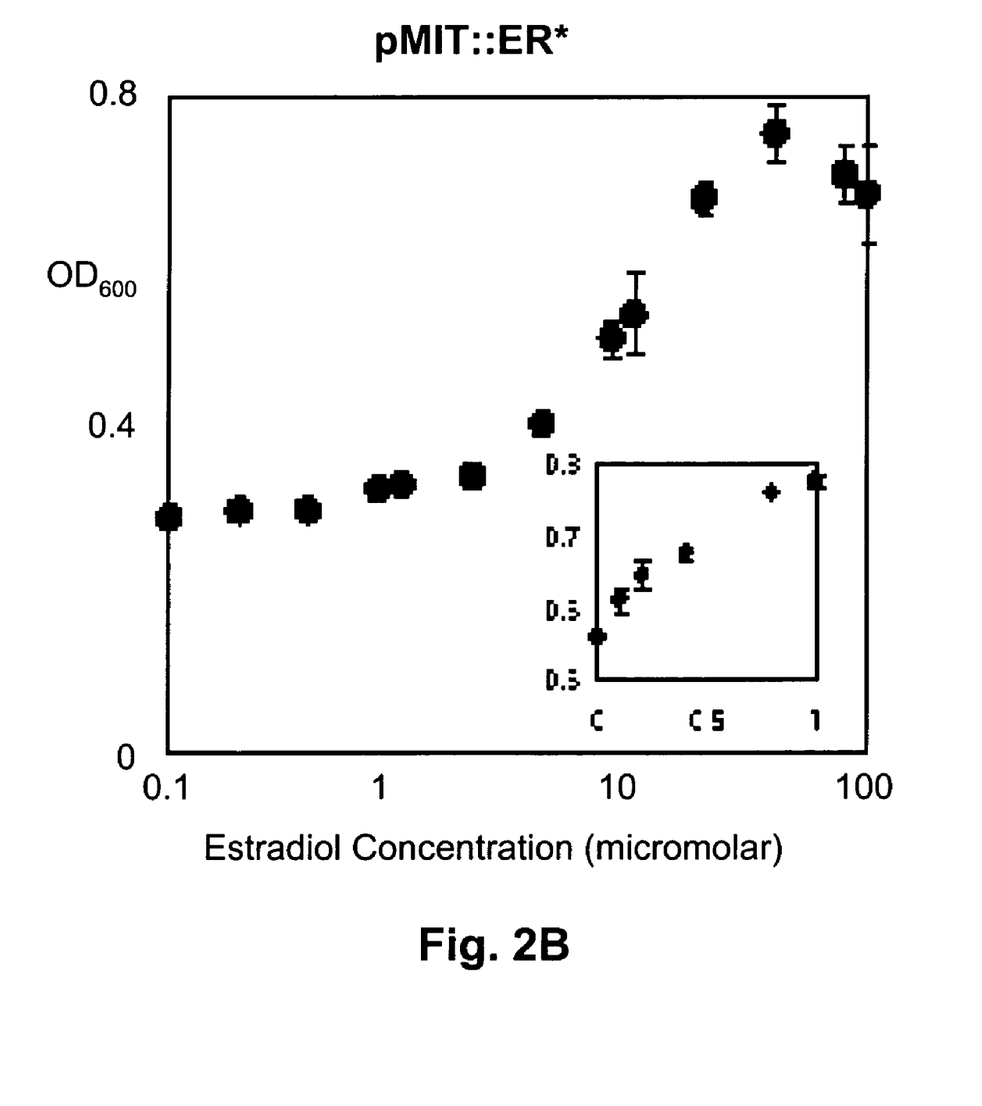
FIG. 2B is a dose-response curve of cells transfected with pMIT::ER* and grown in 5 milliliter cultures of liquid thymineless medium at 34 degrees Celsius in the presence of $E_2$ for 15 hours and 20 hours (inset). Varying concentrations of estrogen were dissolved in dimethylsulfoxide to allow precise control of dosing. Experiments were carried out in duplicate and errors bars represent one standard deviation from the mean value.
Figure 2C:
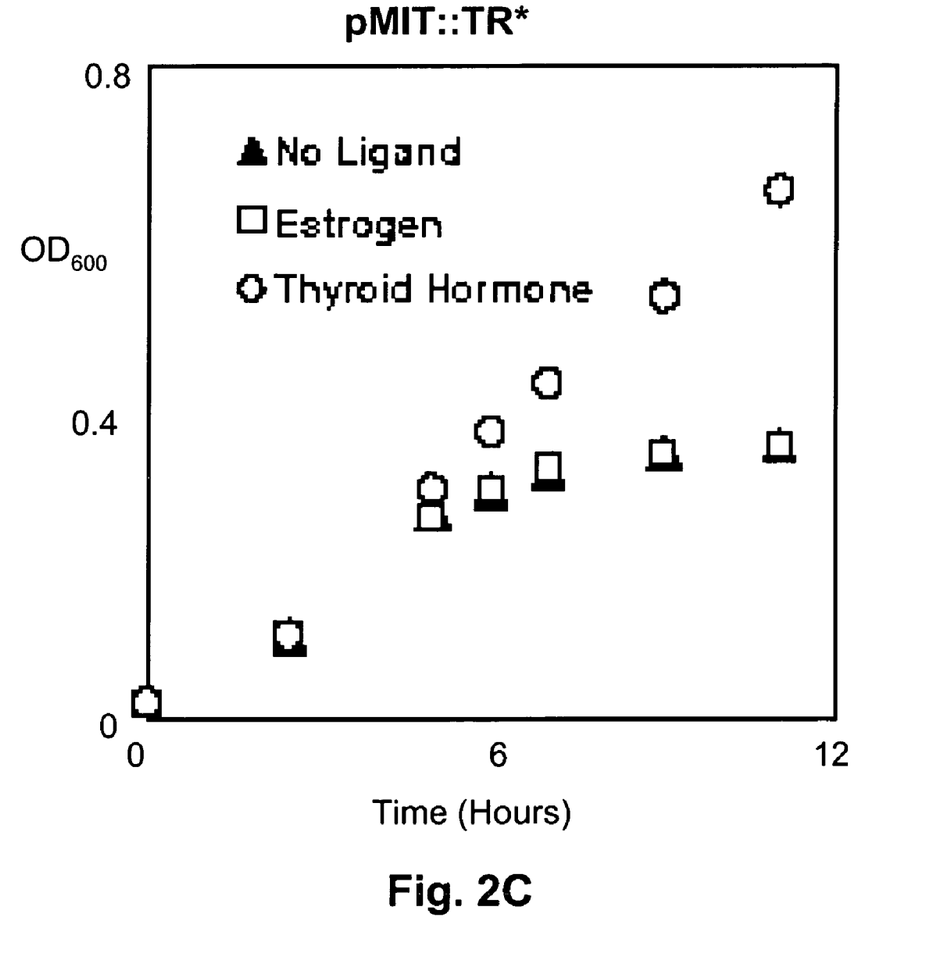
FIG. 2C is a graph that depicts ligand effects on the growth phenotypes of cells harboring pMIT::TR* in 50 milliliter cultures of liquid thymineless medium at 34 degrees Celsius.

Cells transfected with pMIT::ER* and incubated at room temperature exhibited TS$^+$ growth phenotypes in liquid thymineless medium in the presence and absence of $E_2$. However, when the temperature was increased to 30 degrees Celsius, cells retained a TS$^+$ phenotype, but growth was enhanced in the presence of estrogen. At 34 degrees Celsius, cells were able to grow in thymineless liquid medium only in the presence of $E_2$ with a half-maximal effective concentration ($EC_{50}$) of approximately 8 micromolar and an apparent estrogen detection limit of 500 nanomolar, as shown in FIGS. 2A and B. Longer incubation times allowed detection of estrogen at lower concentrations (FIG. 2B, inset). To verify that the observed growth phenotypes were specifically due to differences in TS activity and not to a general metabolic effect of estrogens, the growth medium was supplemented with thyrnine to rescue TS$^-$ and weakly TS$^+$ cells. In a thymine-rich medium, TS$^+$ phenotypes were observed at all temperatures and showed no sensitivity to the presence of hormone.

To investigate the ability of the system to work with other receptors, the ER LBD was replaced with the LBD of the human thyroid hormone receptor beta (TR) to form plasmid pMIT::TR* (FIG. 1A-3). Cells transformed with this plasmid and incubated in liquid thymineless medium at 34 degrees Celsius were able to grow only in the presence of the natural thyroid hormone 3,3',5'-triiodo-L-thyronine ($T_3$), but were insensitive to the presence of estrogen, as shown in FIG. 2C. Similarly, cells carrying pMIT::ER* were insensitive to the presence of $T_3$, as shown in FIG. 2A. This indicates that ligand-receptor interactions and TS activation are specific events.

Figure 2D:
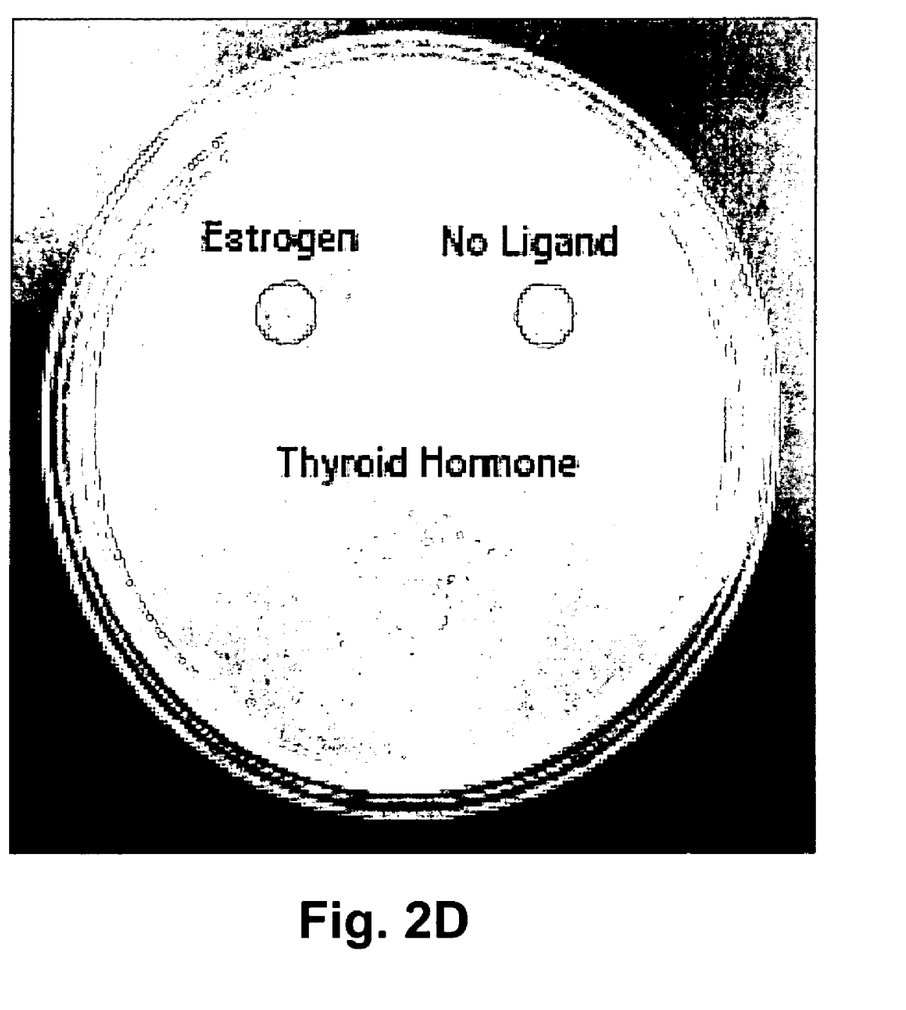
FIG. 2D is an image that depicts ligand effects on the growth phenotypes of cells harboring pMIT::TR* and incubated on thymineless agar plates at 30 degrees Celsius for approximately 50 hours. In the experiments corresponding to FIGS. 2A and 2C estrogen ($E_2$) and thyroid hormone ($T_3$), respectively, were added at 10 micromolar concentrations. In the experiment corresponding to FIG. 2D, the paper disks applied were allowed to saturate in 10 millimolar solutions of estrogen and thyroid hormone prior to applying them to the medium.

The sensitivity and selectivity of the thyroid hormone sensor was further demonstrated by growth phenotype on selective agar plates, as shown in FIG. 2D. In this case a lawn of cells was plated onto thymineless medium and exposed to small paper disks impregnated with either estrogen or thyroid hormone. After incubation at 30 degrees Celsius for approximately 50 hours, clear colonies were observed around the $T_3$-containing disk, while no colonies could be observed surrounding the estrogen-containing or the ligand-free disks.

In order to investigate the structural/functional role of the intein in the constructed sensor protein, the splicing domain was genetically deleted and the resulting inteinless MBP-ER-TS fusion was expressed and tested for hormone-dependent behavior. Although hormone-enhanced cell growth could still be detected with this construct at temperatures below 30 degrees Celsius, the overall cell growth was significantly decreased and the impact of hormone binding on growth phenotypes was much less pronounced compared to that of the intein-containing fusion. These results demonstrate that the intein splicing domain is required for the hormone-sensing efficiency of the constructed fusion protein. Without being bound by any particular theory of operation, it is believed that this is because the intein possesses an ability to "lock" an otherwise poorly folded receptor in a well folded, native-like conformation that allows it to retain its binding characteristics in the bacterial cytoplasm.

Screening of Hormone Analogues

Figure 3A:
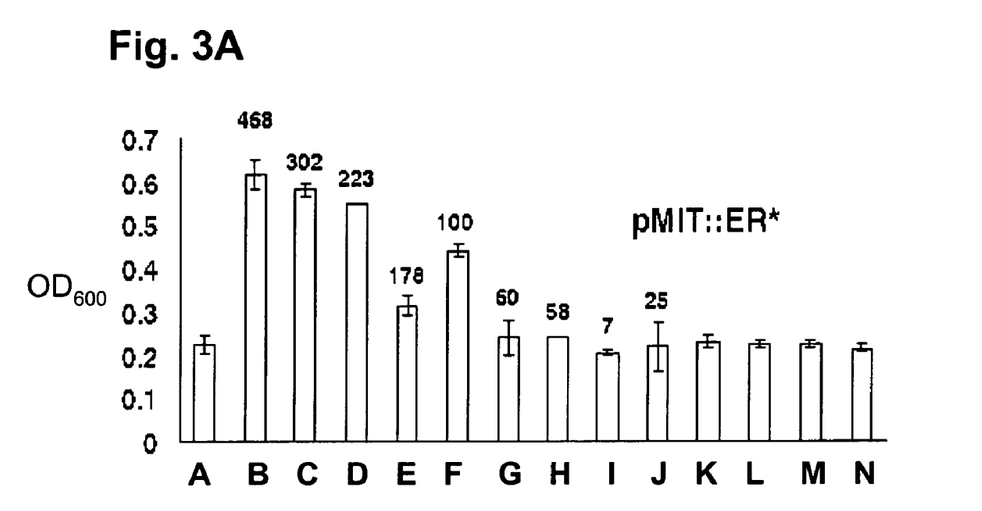
FIGS. 3A and 3B, is a pair of bar graphs that indicate bacterial sensor growth in a screening assay for estrogen and thyroid hormone analogues. E. coli D1210 (delta)thyA cells carrying either pMIT::ER* (FIG. 3A) or pMIT::TR* (FIG. 3B) were grown for 15 hours in 5 milliliter cultures of liquid thymineless medium at 34 degrees Celsius in the presence of compounds that are known to bind to ER.
Figure 3B:
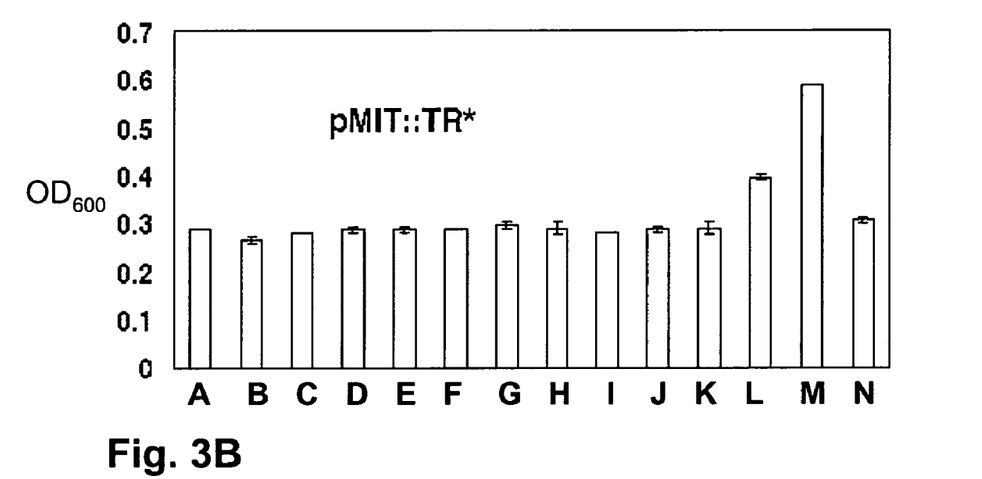

The ability to reliably detect the presence of hormone mimics among thousands of test compounds is an important prerequisite for a hormone screening system. Cells carrying either pMIT::ER* or pMIT::TR* were tested for growth in the presence of a small library of estrogen, thyroid hormone, and analogues. Cells harboring pMIT::ER* were sensitive only to the presence of estrogen analogues, while compounds that are known to bind to TR ($T_3$ and 3,3',5-triiodothyroacetic acid, "Triac") were able to enhance growth only in cell cultures expressing the TR fusion, as shown in FIG. 3. Non-binding compounds, such as progesterone, had no effect on cell growth in either case. Different compounds were able to induce variable levels of cell growth. In general, compounds with higher receptor binding affinities exhibited stronger growth effects. For example, Triac has been shown to have a 3- to 4-fold greater binding affinity for TR than $T_3$ both in vivo and in vitro (Takeda et al., 1995, J. Clin. Endocrinol. Metab. 80:2033-2040). Addition of Triac to cell cultures resulted in a much more pronounced enhancement of cell growth than did addition of $T_3$, as shown in FIG. 3B. In the case of ER a similar trend was observed. Levels of pMIT::ER*-transformed cell growth correlated well with reported in vitro measurements of binding affinities of the tested estrogen analogues, as shown in FIG. 3A.

Detection of Antagonism

Figure 4:
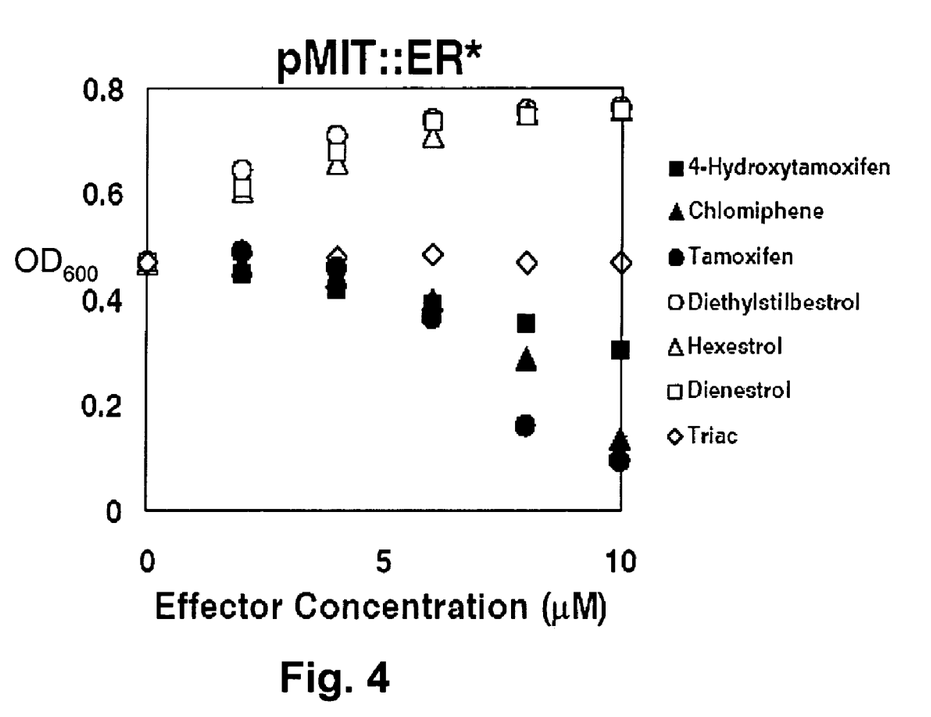

Many commercially available pharmaceuticals that target the estrogen receptor, such as tamoxifen and raloxifene, inhibit specific hormonal responses (Riggs et al., 2003, N. Engl. J. Med. 348:618-629). To assess the ability of the pMIT::ER* strain to detect such antagonistic phenomena, the ER fusion was expressed in liquid thymineless medium at 34 degrees Celsius in the presence of $E_2$ and combined with increasing concentrations of agonistic, antagonistic, or non-binding compounds. The results of these experiments are depicted in FIG. 4. Addition of the non-binding thyroid hormone analogue Triac had no impact on cell growth. However, growth was significantly affected by the presence of estrogen agonists and antagonists. In all cases, the addition of known estrogen agonists had an additive effect on cell growth, and addition of known antagonists inhibited growth.

When cells were transfected with the pMIT::TR* vector and incubated in liquid thymineless medium at 34 degrees Celsius in the presence of $T_3$, cell growth increased upon addition of Triac, but was unaffected by estrogen agonists or antagonists. Furthermore, when either fusion was expressed in a thymine-rich control medium with the same compounds added, significant ligand effects on growth phenotypes could no longer be detected. These results demonstrate that the ability of the tested antagonist compounds to neutralize the effects of $E_2$ on the TS activity of the ER fusion do not arise from general toxicity effects. Remarkably, the inhibitory effects of tamoxifen, 4-hydroxytamoxifen, and chlomiphene were observed not only with $E_2$, but with all of the estrogen agonists tested (diethylstilbestrol, hexestrol, and dienestrol). The inteinless MBP-ER-TS fusion could recognize tamoxifen and chlomiphene as estrogen antagonists but, 4-hydroxytamoxifen was found to behave as an estrogen super-agonist in this context.

Discussion

The experiments described in this example report a bacterial hormone binding sensor made by transforming E. coli cells with a fusion protein. The fusion protein includes a solubility-enhancing maltose binding protein (MBP) domain fused to the amino-terminal end of the amino-terminal splicing region of an inactivated intein having the ligand-binding domain (LBD) a human hormone receptor fused between its amino- and carboxyl-terminal splicing regions in place of the endonuclease domain of the naturally-occurring form of the intein. The fusion protein has an auxotroph-relieving protein domain (a thymidylate synthase (TS) domain in this example) activatably fused to the carboxyl-terminal end of the carboxyl-terminal splicing region of the intein. Binding of a ligand (i.e., the hormone or an agonist of the hormone) of the receptor protein activated the fused TS moiety, enhancing growth of otherwise thymine-auxotrophic bacteria on a thymineless medium. Presence of a hormone antagonist of the binding protein reduced the growth enhancement.

The sensor system reported in this example can be used to detect the presence of human hormones and hormone-like compounds by changes in growth phenotype of bacterial cells. The ligand-binding domains of the human estrogen receptor alpha and the thyroid hormone receptor beta were inserted into this sensor and used to screen a small library of estrogen and thyroid hormone analogues. The system successful differentiated members of the library that are known to bind to each corresponding receptor. Weaker ligands of the ER had smaller impacts on cell growth. However, longer incubation times facilitated detection of nearly all of estrogen agonists, and all of the estrogen antagonists were readily detected in the presence of agonists. Quantitative information could be derived about ligand-receptor affinity by observing the relative impact of each hormone analogue on cell growth.

Current tools for the discovery of novel compounds with the ability to regulate nuclear receptor endocrine pathways include in vitro ligand-binding assays with radiolabeled compounds, yeast transcriptional assays, and animal cell-based models. However, animal models are complex and unwieldy, while simpler in vitro assays are designed to report only the binding affinity of a test compound.

The yeast S. cerevisiae has been a simple and efficient cell host for studying the hormone-dependent gene transcription machinery of higher eukaryotes, but it has been ineffective in recognizing the biologically relevant role of test compounds. In general, yeast-based assays have been unsuccessful in reliably demonstrating inhibitory effects of known hormone antagonists of nuclear receptors (Joyeux et al., 1997, Anal. Biochem. 249:119-130). For example, a yeast-based transcriptional assay that successfully recognizes the antagonistic activity of 4-hydroxytamoxifen has been reported, but failed to recognize antagonistic activity of other partial or pure estrogen antagonists (Liu et al., 1999, Biol. Chem. 380:1341-1345). Similarly, another gene transcription assay in yeast was able to detect inhibitory effects only for the partial estrogen antagonist nafoxidine (Pham et al., 1991, Proc. Natl. Acad. Sci. USA 88:3125-3129).

In the system described in this example, antagonistic behavior was detected and differentiated from that of estrogen agonists in all cases tested. Bacterial cells possess much simpler import-export machinery for chemical compounds than do yeast or other eukaryotic cells. Bacterial systems can therefore allow antagonists to accumulate in the cytoplasm and interact with the receptor-agonist complex more readily than in yeast cells.

Considering the simplicity of the design of the biosensor described in this example, it is surprising that bacterial growth was consistent with the biological action of these compounds in higher eukaryotes. This represents a significant advance over existing simple screening systems, and appears to be the first system capable of exhibiting a general sensitivity to a variety of estrogen antagonists outside of a mammalian cell host.

It has been previously reported that the activity of several proteins can be modulated by simple end-to-end fusion with steroid-binding domains (Mattioni et al., 1994, Methods Cell Biol. 43(Pt A):335-352; Picard, 2000, Methods Enzymol. 327:385-401). In these fusions, activity appears to be modulated by association of the Hsp90 chaperone protein, which binds the partially unfolded binding domain in the absence of the ligand and sterically blocks the attached protein. Dissociation of Hsp90 is induced by ligand binding, which stabilizes the binding domain and activates the fusion partner (Mattioni et al., 1994, Methods Cell Biol. 43(Pt A):335-352; Picard, 2000, Methods Enzymol. 327:385-401). However, this mechanism cannot explain the hormone-dependent behavior of the TR fusion in this system, since the thyroid hormone receptor is not a substrate for such chaperones (Pratt et al., 1997, Endocr. Rev. 18:306-360). In addition, very recent results using purified samples of the sensor proteins described in this study confirm that the catalytic activity of the TS enzyme can be directly modulated by hormone binding in vitro in the absence of chaperones.

Detection of antagonistic activity, particularly with weakly binding antagonists, implies that simple ligand-induced stabilization is not sufficient to describe the behavior of the sensor system described in this example. These properties suggest that the hormone-binding domain is able to adopt a stable fold regardless of the presence of ligand, thus allowing hormone effects to be correctly reflected.

Crystallographic studies of the nuclear receptors have revealed that the carboxyl-terminal regions of their LBDs undergo large conformational changes upon hormone binding (Bourguet et al., 2000, Trends Pharmacol. Sci. 21:381-388). Without being bound by any particular theory of operation, it is proposed that these conformational changes affect the general configuration of the chimeric sensor protein described in this example, which is reflected in changes in TS activity. A similar mechanism has been previously hypothesized by others to explain the dexamethasone-regulated enzymatic activity of a DHFR fusion with the hormone-binding domain of the glucocorticoid receptor (Israel et al., 1993, Proc. Natl. Acad. Sci. USA 90:4290-4294).

It has also been suggested that intein fusions to the amino-terminus of the TS enzyme sterically block its homodimerization, which is required for its activation (Wood et al., 1999, Nat. Biotechnol. 17:889-892). Without being bound by any particular theory of operation, it is hypothesized that the conformational changes that take place at the binding domain upon hormone binding to the fusion proteins described in this example are transmitted to the carboxyl-terminal intein splicing domain and cause rearrangement of some of its structural features. In this perturbed intein domain structure, blockage of TS dimerization is partially alleviated, allowing an increase in TS function. This increase is readily detected due to the high sensitivity and tunable nature of the TS reporter system. Conformational changes of the ligand-binding domains of nuclear receptors induced by hormone binding have been exploited for the construction of chimeric inteins having splicing activity that is allosterically regulated by the presence of small-molecule ligands (Buskirk et al., 2004, Proc. Natl. Acad. Sci. USA 101:10505-10510; Skretas et al., 2005, Protein Sci. 14:523-532).

In order to further examine the structural and functional role of the intein splicing domains in the sensor proteins described in this example, an inteinless MBP-ER-TS fusion was constructed and tested for hormone-dependent behavior. Although hormone-enhanced cell growth could still be detected in this context at temperatures below 30 degrees Celsius, the overall cell growth was significantly decreased and the impact of hormone binding on growth phenotypes was not as pronounced. Furthermore, 4-hydroxytamoxifen behaved as an estrogen super-agonist for this inteinless fusion protein, in contradiction to the antagonistic effects it exhibited in the original fusion proteins. These results support the notion that the intein splicing domain has a significant role in stabilizing the hormone binding domain in a properly folded state.

Ability of one or both intein splicing domains to function as a stabilization domain may arise from the two-domain native structure of inteins and evolution of inteins as mobile genetic elements (Derbyshire et al., 1997, Proc. Natl. Acad. Sci. USA 94:11466-11471). The splicing domain has been previously found to be tolerant to foreign domain insertions (Gangopadhyay et al., 2003, Biochim. Biophys. Acta 1619:193-200; Wu et al., 2002, Nucleic Acids Res. 30:4864-4871; Fitzsimons-Hall et al., 2002, J. Mol. Biol. 323:173-179; Buskirk et al., 2004, Proc. Natl. Acad. Sci. USA 101:10505-10510; Skretas et al., 2005, Protein Sci. 14:523-532). Intein mobility requires reliable folding and function in a variety of contexts.

An important result of the work described in this example is that ER LBD could be trivially replaced with TR LBD without loss of ligand-sensing capability and without any mutagenesis requirements. Due to the relative structural homogeneity of the nuclear receptors and the expectation that for all the members of this superfamily similar conformational changes take place upon hormone binding (Bourguet et al., 2000, Trends Pharmacol. Sci. 21:381-388), one expects that many, if not all, of proteins in this superfamily will have LBDs that perform in this system in a manner analogous to the ER and TR LBDs. For example, the LBD of the beta subtype of the ER can be used in place of the LBD of the alpha subtype described herein.

The ability of the system described in this example to detect a variety of receptor-ligand interactions, combined with the simplicity and genetic engineering capability of *E. coli* and other bacteria suggests many possible applications for this system. Such applications include sensing and identification of novel hormone-like compounds with possible therapeutic properties, the discovery of new receptors, and potentially the directed evolution of new peptide and small-molecule drugs in bacterial hosts.

Cloning a LBD of an orphan nuclear receptor in place of the ER or TR LBDs described in this example permits the system to be used to search for ligands that bind to the orphan receptor and to assign a function to the receptor (Giguere, 1999, Endocr. Rev. 20:689-725). Lately, binders for some of these receptors have been identified (Stehlin-Gaon et al., 2003, Nat. Struct. Biol. 10:820-825; Coward et al., 2001, Proc. Natl. Acad. Sci. USA 98:8880-8884; Kliewer et al., 1998, Cell 92:73-82), and a functional role has been proposed for them (Kliewer et al., 1998, Cell 92:73-82; de Urquiza et al., 2000, Science 290:2140-2144; Kamei et al., 2003, Proc. Natl. Acad. Sci. USA 100:12378-12383). Association of these receptors with important aspects of the human development and metabolism has attracted considerable attention to the investigation of the orphan receptors' signaling pathways and their potential for drug discovery. High-throughput insertion of LBDs for genes of unknown function and screening of their products against large compound libraries could provide identify physiological ligands of the proteins encoded by the genes.

The system described in this example can be used to evolve receptors to exhibit engineered binding characteristics. A natural receptor can be subjected to directed (or random) evolution, and variants with the ability to respond to a synthetic ligand, for example, can be selected. It was demonstrated that an estrogen receptor can be converted quite trivially to an androgen-like receptor with the ability to bind testosterone with good affinity (Chen et al., 2004, J. Biol. Chem. 279:33855-33864). Engineered receptors with the ability to bind to a non-natural compound selected by the researcher can potentially be used in gene therapy and other applications. The simplicity of the constructed sensor protein suggests further that limits on rational protein design capability may be partially overcome by highly sensitive activity assays, which may allow a more general use of chimeric sensors in future research applications.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A fusion protein comprising
   i) a ligand-binding domain (LBD) of a protein fused between the amino- and carboxyl-terminal splicing regions of an intein in place of most or all of the endonuclease domain of the naturally-occurring form of the intein, such that the amino acid sequence of the intein differs from the amino acid sequence of the naturally-occurring form of the intein that the ability of the intein to cleave and splice a polypeptide in which the intein occurs is eliminated and
   ii) a bacterial auxotroph-relieving protein domain (ARPD) activatably fused, by way of one of the amino- and carboxyl-terminal splicing regions of the intein, to the LBD in such a manner that the auxotrophy-relieving function of the ARPD is greater when a ligand is bound to the LBD than when a ligand is not bound to the LBD.

2. The fusion protein of claim 1, wherein the protein is a membrane-bound receptor protein.

3. The fusion protein of claim 1, wherein the protein is an integral membrane-bound receptor protein.

4. The fusion protein of claim 1, wherein a LBD of a nuclear receptor protein is fused between the amino- and carboxyl-terminal splicing regions.

5. The fusion protein of claim 1, wherein a LBD of a nuclear hormone receptor protein is fused between the amino- and carboxyl-terminal splicing regions.

6. The fusion protein of claim 5, wherein the nuclear hormone receptor protein is an estrogen receptor.

7. The fusion protein of claim 6, wherein the estrogen receptor is one of human estrogen receptors alpha and beta.

8. The fusion protein of claim 5, wherein the nuclear hormone receptor protein is a thyroid hormone receptor.

9. The fusion protein of claim 8, wherein the thyroid hormone receptor is human thyroid hormone receptor beta.

10. The fusion protein of claim 1, wherein the bacterial ARPD is a functional domain of a protein required for a function selected from the group consisting of purine uptake, purine metabolism, pyrimidine uptake, pyrimidine metabolism, amino acid uptake, and amino acid metabolism.

11. The fusion protein of claim 1, wherein the bacterial ARPD is a functional domain of thymidylate synthase.

12. The fusion protein of claim 1, wherein the bacterial ARPD is a functional domain of dihydrofolate reductase.

13. The fusion protein of claim 1, wherein the intein is the Mtu RecA intein.

14. The fusion protein of claim 1, further comprising a solubility-enhancing protein domain, wherein the solubility-enhancing protein domain is fused, by way of the other of the amino- and carboxyl-terminal splicing regions of the intein, to the LBD.

15. The fusion protein of claim 14, wherein the solubility-enhancing protein domain is fused to the amino terminal splicing region of the intein.

16. The fusion protein of claim 14, wherein the solubility-enhancing protein domain is *E. coli* maltose-binding protein.

17. The fusion protein of claim 1, wherein the LBD is fused to the carboxyl-terminal end of the amino-terminal splicing region of the intein and to the amino-terminal end of the carboxyl-terminal splicing region of the intein and wherein the ARPD is fused to the carboxyl-terminal end of the carboxyl-terminal splicing region of the intein.

18. The fusion protein of claim 17, further comprising a solubility-enhancing protein domain fused to the amino-terminal end of the amino-terminal splicing region of the intein.

19. An expression cassette expressible in a bacterial cell, the cassette comprising a promoter/regulatory region operably linked with a coding region encoding
   i) a ligand-binding domain (LBD) of a protein fused between the amino- and carboxyl-terminal splicing regions of an intein in place of most or all of the endonuclease domain of the naturally-occurring form of the intein, such that the amino acid sequence of the intein differs from the amino acid sequence of the naturally-occurring form of the intein that the ability of the intein to cleave and splice a polypeptide in which the intein occurs is eliminated and
   ii) a bacterial auxotroph-relieving protein domain (ARPD) activatably fused, by way of one of the amino- and carboxyl-terminal splicing regions of the intein, to the LBD in such a manner that the auxotrophy-relieving function of the ARPD is greater when a ligand is bound to the LBD than when a ligand is not bound to the LBD.

20. A method of comparing the ability of a plurality of sequence variants of a ligand-binding domain (LBD) to bind a ligand, the method comprising separately expressing fusion proteins in populations of auxotrophic host bacteria, each fusion protein comprising
   i) a LBD of a protein fused between the amino- and carboxyl-terminal splicing regions of an intein in place of most or all of the endonuclease domain of the naturally-occurring form of the intein, such that the amino acid seciuence of the intein differs sufficiently from the amino acid sequence of the naturally-occurring form of the intein that the ability of the intein to cleave and splice a polypeptide in which the intein occurs is substantially eliminated and ii) a bacterial auxotroph-relieving protein domain (ARPD) activatably fused, by way of one of the amino- and carboxyl-terminal splicing regions of the intein, to the LBD in such a manner that the auxotrophy-relieving function of the ARPD is greater when a ligand is bound to the LBD than when a ligand is not bound to the LBD; and observing at least one trait of the bacteria selected from the group consisting of survival, growth, and proliferation, whereby exhibition of the trait in the presence of the compound is correlated with binding of the compound with the LBD variant.

21. The expression cassette of claim 19, wherein the promoter/regulatory region includes a constitutive bacterial promoter.

22. The expression cassette of claim 19, wherein the promoter/regulatory region includes an *E. coli* lac operator region having a G to A substitution 16 bases downstream of the TATAA motif of the lac promoter.

23. A host bacterium transformed with the expression cassette of claim 19.

24. The host bacterium of claim 23, wherein the host bacterium exhibits auxotrophy relieved by the ARPD.

25. A method of assessing binding of a compound with a LBD of a protein, the method comprising contacting the host bacterium of claim 23 and the compound in the presence of an auxotrophic medium and observing at least one trait of the bacterium selected from the group consisting of survival, growth, and proliferation, whereby exhibition of the trait in the presence of the compound is correlated with binding of the compound with the ligand-binding domain.

26. The method of claim 25, wherein the host bacterium and the compound are contacted in the presence of a known ligand of the LBD, whereby exhibition of the trait in the presence of the compound is correlated with ability of the compound to modulate binding of the known ligand with the LBD.

* * * * *